United States Patent [19]

Hawkins, Jr.

[11] Patent Number: 4,874,376

[45] Date of Patent: Oct. 17, 1989

[54] NEEDLE GUIDE ASSEMBLY

[76] Inventor: Irvin F. Hawkins, Jr., 1600 Archer Rd., Gainesville, Fla. 32610

[21] Appl. No.: 37,331

[22] Filed: Apr. 13, 1987

[51] Int. Cl.$^4$ .............................................. A61M 5/00
[52] U.S. Cl. ................................... 604/165; 128/772
[58] Field of Search ............................. 604/164–170, 604/158, 264, 280, 51; 128/657, 658, 772

[56] References Cited

U.S. PATENT DOCUMENTS

| | | | |
|---|---|---|---|
| 4,230,123 | 10/1980 | Hawkins | 604/165 X |
| 4,445,883 | 5/1984 | Bodicky | 604/165 |
| 4,772,264 | 9/1988 | Cragg | 604/165 |

Primary Examiner—Stephen C. Pellegrino
Attorney, Agent, or Firm—Emrich & Dithmar

[57] ABSTRACT

A needle guide assembly for placement of tubular surgical instruments within a human or animal body includes a short locator needle assembled within a needle guide outer cannula for penetrating the body to locate a target area, the locator needle being removable from the needle guide assembly permitting a long guide wire to be inserted through the needle guide outer cannula into the body to locate its distal end at the target area, the needle guide outer cannula being crimped to the guide wire to form a guide assembly for advancing the tubular surgical instrument to the target area.

24 Claims, 2 Drawing Sheets

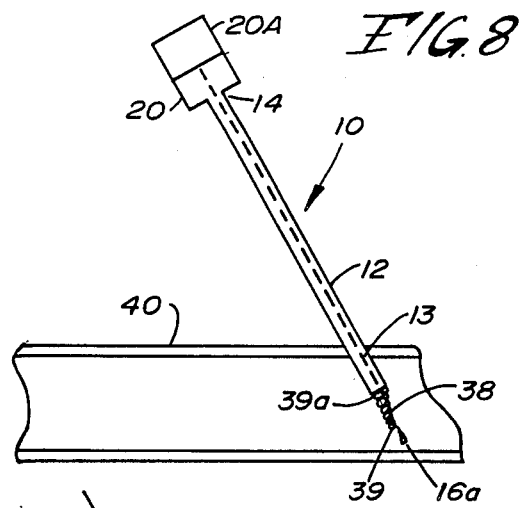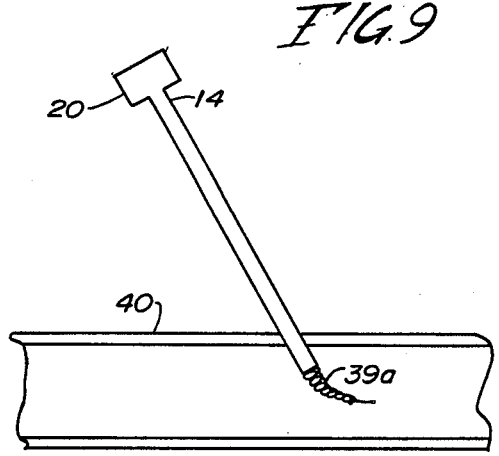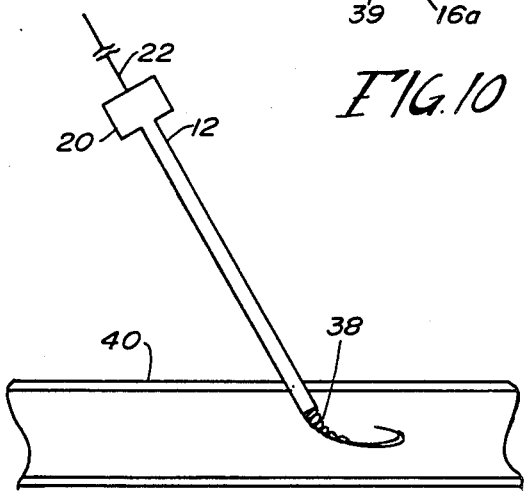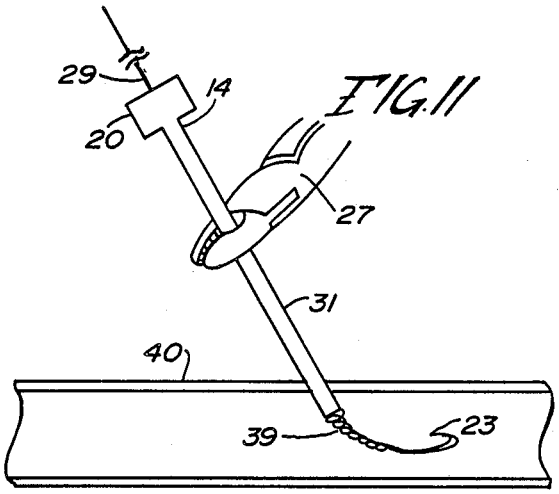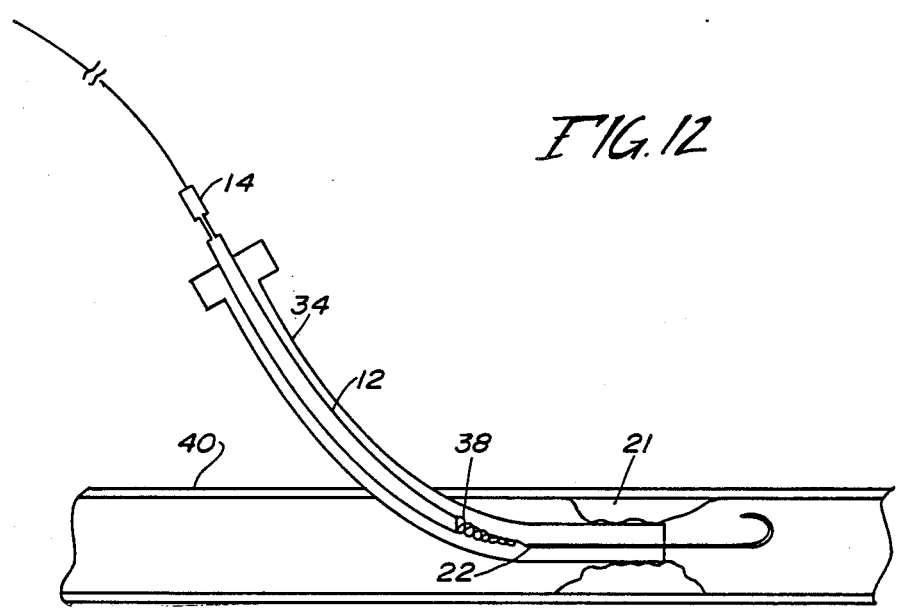

NEEDLE GUIDE ASSEMBLY

BACKGROUND OF THE INVENTION

The present invention relates to a novel needle guide assembly which permits the needle guide outer cannula to function as a localizing needle and as a guide wire for placement of a surgical instrument or catheter at or within the target area to be examined.

The use of a small needle system (21-23 gauge) for placement of percutaneous nephrostomy tubes, abscess drainages, biliary endoprotheses, translumbar aortography or normal structure such as the kidney or an artery have become routine in the past several years because the small gauge needle can pass through most of the human anatomy without significant damage to the anatomy. However, a needle of this size is too small to permit adequate drainage for therapeutic purposes and it is too small to extract samples of infected material or suspect structure for diagnostic purposes.

Thus, the capturing of cells through such a small needle is, at times, wholly inadequate for a definitive diagnosis. In 1979, a new system was introduced in which a long fine needle was used to localize the target. Subsequently, larger needles, catheters or other instruments were advanced over this needle into the target. Thus, larger samples could be obtained by the larger needle and catheters large enough for adequate drainage could be placed. In the average patient a 40 to 50 centimeter needle is required to place short drainage catheters and biopsy needles, and 50 to 200 centimeter needles are required to place longer angiographic catheters. This length is necessary because when the long fine needle is inserted into the body it is necessary that the needle have a length extending outwardly from the skin or surfaces of the anatomy which is greater than the length of the catheter drainage instrument biopsy needle that is going to be positioned over the fine needle for insertion into the body tissue or target area. Because of the occasionally extreme length of such a needle system, it has been suggested that a 21-22 gauge fine needle be utilized to localize or penetrate a particular organ or target. A shorter outer needle or catheter is inserted over this needle into the target. The inner fine needle is removed and a standard guide wire is advanced through the larger needle as in the standard Seldinger technique (1954). During the several steps required to place the larger guide wire, there is a possibility of losing access to the target. Also the standard guide wire is flexible and not near as rigid as the original fine needle which was used for the initial search. If the fine (22 gauge) needle is used with a standard guide wire 0.018 inches (as the standard Seldinger technique), this inner wire is not strong enough to permit single step placement or larger biopsy needles or drainage catheters.

The present invention is directed to an assembly which overcomes these difficulties.

SUMMARY OF THE INVENTION

One object of the present invention is a novel needle guide assembly.

A further object of the present invention is a needle guide assembly, of simple construction, which is easy to use and which permits the placement within a target area of the body of a catheter of any variable length.

Still another object of the present invention is a short needle guide assembly which permits and functions as a localization instrument in identifying a target or area within a body.

Still another object of the present invention is a needle guide assembly which functions as a guide wire for the placement of a catheter of any given length within the target area of a body.

Still another object of the present invention is a novel needle guide assembly which permits the length of the guide assembly to be substantially increased thereby permitting, after localization of the target area within the body, placement of catheter within the target area of the body.

It is still another object of the present invention to provide a novel method of locating medical instruments or catheters within the target area of the body.

The above identified objects of the present invention are accomplished by a novel needle guide assembly which is utilized as a placement tool for placing or guiding tubular surgical instruments or catheters to a target area within a human or animal body. The needle guide assembly includes a needle guide outer cannula, comprised of a hollow tubular member having a distal end and a proximal end and a locator needle or stylus having a distal end and a proximal end. The locator needle is constructed and arranged to be removably positioned within the needle guide outer cannula, with its proximal end located at or adjacent the proximal end of the needle guide to permit and facilitate penetration into the target area of the human or animal body and the positioning of the distal end of the needle guide outer cannula in the precise proximity of the target area within the body. Upon removal of the locator needle from the needle guide outer cannula, a guide wire is inserted into and through the tubular needle guide outer cannula to locate the distal end of the guide wire near or in the target or area within the body. The tip of the guide wire facilitates manueverability of the assembly within the target and guides the assembly for optimum position within the target. Means for securing the needle guide outer cannula to the guide wire is provided to provide a needle guide assembly for advancing a surgical tubular instrument into the target area.

Additionally, a novel method for the placement of surgical tubes into a target area within a human or animal body includes the step of probing the body with a needle guide assembly having a locator needle slidably extending within the needle guide outer cannula to locate the target area within the body. Upon withdrawal of the locator needle from the needle guide outer cannula, a guide wire is inserted through the needle guide outer cannula into the body to locate its distal end at or adjacent the target area. The crimping the needle guide outer cannula to the guide wire to provide a needle guide assembly of sufficient length permits advancing a tubular surgical instrument of a desired length over the needle guide assembly into the target area.

The invention consists of certain novel features and structural details hereinafter fully described, illustrated in the accompanying drawings, and particularly pointed out in the appended claims, it being understood that various changes in the details may be made without departing from the spirit, or sacrificing any of the advantages of the present invention.

DESCRIPTION OF THE DRAWINGS

FIG. 8, illustrates a second embodiment of the present invention of the needle guide assembly having its locator needle assembled within a needle guide outer cannula having a flexible tip thereon, the needle guide assembly shown penetrating an artery or ventricular system in a human body to locate a target area;

FIG. 9, illustrates the needle guide assembly in accordance with FIG. 8 with the locator needle withdrawn permitting the flexible tip of the needle guide outer cannula to orient itself within the artery or ventricular system;

FIG. 10, illustrates a guide wire being inserted through the needle guide outer cannula in accordance with the present invention into the artery or ventricular system to locate its distal end near the target area within the vascular artery;

FIG. 11, illustrates crimping the needle guide outer cannula to the guide wire to form the needle guide assembly in accordance with the present invention; and FIG. 12, illustrates use of the guide assembly in accordance with the present invention to advance a tubular surgical instrument or catheter into the target area being examined.

DESCRIPTION OF THE PREFERRED EMBODIMENTS

Figure 2:
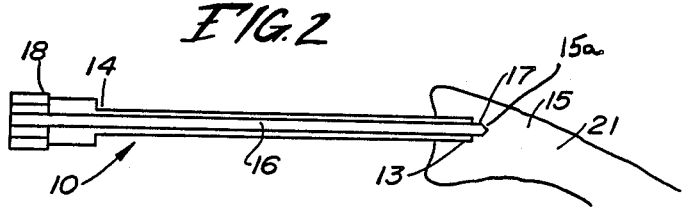
FIG. 2, illustrates the needle guide assembly in accordance within the present invention having its locator needle assembled with the needle guide outer cannula, the needle guide assembly shown penetrating the body in the proximity of a target area.
Figure 3:
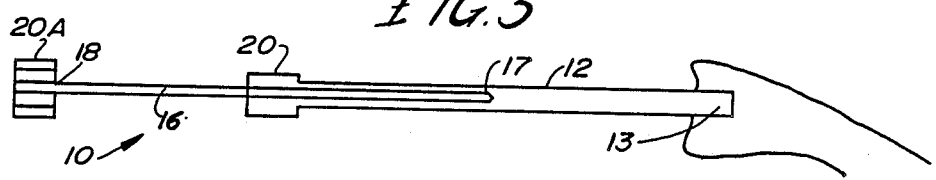
FIG. 3, is a view similiar to FIG. 2, illustrating the locator needle being withdrawn from the needle guide outer cannula after the distal end of the needle guide assembly has penetrated the body in the proximity of a target area.

In the drawings, like numeral have been used throughout the several views to designate the same or similiar parts of the needle guide assembly 10 in accordance with the present invention is disclosed and described. The needle guide assembly 10 is for use as a localizing instrument to identify or localize a particular target area within the body and for use as a guide wire assembly for the placement of surgical instruments or catheters, including nephrostomy tubes, abscess drainages, biliary endoprotheses and translumbar aortography. As shown in FIGS. 2-7, the needle guide assembly 10 is comprised of a short needle guide outer cannula member 12, which is tubular in shape, having a distal end 13 and a proximal end 14. The short needle guide assembly 10, preferably, has a needle guide outer cannula of approximately 15 to 20 centimeters in length and a preferred size of 20-22. A locator needle or stylus 16 having a distal end 17 and a proximal end 18 is removably and slidably positioned within the needle guide outer cannula 12, as shown in FIG. 2 and 3. The locator needle or stylus 16 corresponds in length to that of the outer cannula and is, preferably, a length of approximately 15 to 20 centimeters. The locator needle or stylus 16 has a sharp piercing tip 15a at its distal end.

Both the proximal end 14 of the outer cannula 12 and the proximal end 18 of the locator needle or stylus 16 include locating hubs 20 and 20A, respectively, thereon, which are used for initial needle placement into the target area 21 of the body. Incorporated herein by reference is my U.S. Pat. No. 4,230,123, which issued Oct. 28, 1980, which describes the general structure of hubs 20 and 20A that are attached to the proximal end 14 of the outer cannula 12 and the proximal end 18 of the locator needle or stylus 16 to connect the same together during insertion and manuevering of the needle guide assembly 10 into the target area and for locking the proximal end 18 of locator stylus 16 to the proximal end 14 outer cannula 12, as described by that patent. Specifically, male hub 20A is fixedly mounted to the locator needle or stylus 16 and female hub 20 is loosely slidably mounted to the outer cannula 12. The hub 20A is adapted to be fastened by screw threads (not shown) into hub 20, with an O-ring positioned there between. Upon unscrewing of hub 20A from hub 20, the locator needle 16 may be withdrawn from the outer cannula 12, and the hub 20 on the outer cannula 12 may be removed, as will herein after be described.

The locator needle or stylus 16 is constructed and arranged to be removably and slidably positioned within the needle guide outer cannula 12, with its distal end 17 and the tip 16a thereof projecting from the distal end 13 of the outer cannula 12 to facilitate penetration of the body and the positioning of the distal end of the needle guide outer cannula in close proximity to the target area 21 within the body. The position of the distal end 17 of the locator needle or stylus 16 and the outer cannula 12 and its distal end within the target area can be confirmed using orthogonal views and the injection of contrast dye through the needle guide outer cannula 12, as desired, or the return of any body substance (blood, urine) after withdrawal of the guide wire from the outer cannula.

After the proper positioning of the outer cannula and locator needle 16 within the target area, as shown in FIG. 2, the locator needle or stylus 16 is detached from the outer cannula by unscrewing hub 20A from hub 20, as described above, and is then slidably removed from the outer cannula member 12, as shown partially in FIG. 3.

Figure 4:
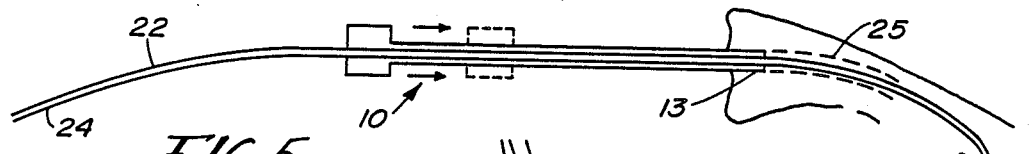
FIG. 4, illustrates a guide or torque wire being inserted through the needle guide outer cannula into the body to locate its distal end near or adjacent the target area and then advancing the needle guide outer cannula and guide wire further into the body to pinpoint and locate the target area.
Figure 5:
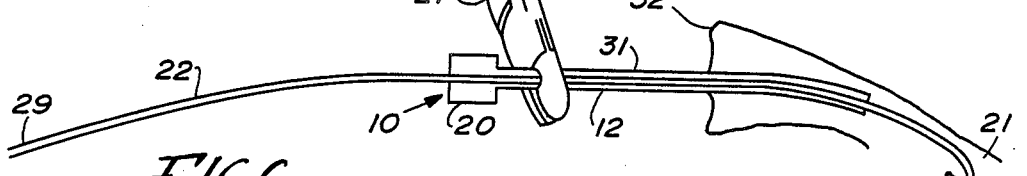
FIG. 5, illustrates crimping the needle guide outer cannula to the guide wire to form the guide wire assembly in accordance with one embodiment of the present invention.
Figure 6:
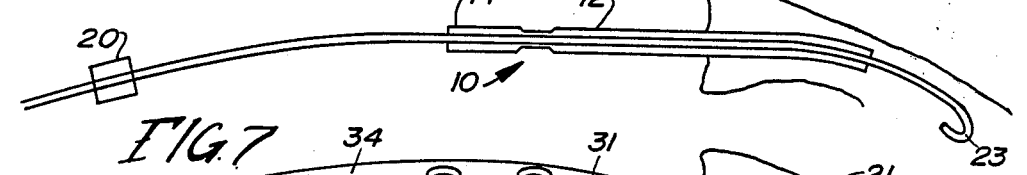
FIG. 6, illustrates removal of the hub from the needle guide outer cannula following formation of the guide assembly in accordance with the present invention, as shown in FIG. 5.

When the locator needle or stylus 16 has been completely removed from the outer cannula 12, an elongated guide wire 22 is inserted within the outer cannula member 12 into the target area 21. The length of the guide wire may be any length exceeding the length of the outer cannula 12 and is preferably a length in excess of twice the length of the inserted surgical instrument. In accordance with one embodiment the guide wire 22 includes a flexible floppy distal end 23 and a proximal end 24. However guide wires with other tip configurations may be used. The elongated guide wire or torque wire 22 is advanced within the outer cannula member 12 as shown in FIG. 4, until the flexible distal end 23 extends beyond the distal end 13 of the outer cannula 12. If necessary, the needle guide outer cannula 12 may be advanced forwardly over the guide or torque wire 22 to a position as shown by the dotted lines 25 in FIG. 4.

When optimal positioning of the needle guide outer cannula 12 and the elongated guide or torque wire 22 has been achieved within the target area 21, a crimping tool 27 is utilized to concentrically compress the needle guide outer cannula about and to the guide or torque wire 22 to provide a needle guide assembly 10 comprised of an elongated external wire guide component portion 29 and a short needle guide outer cannula portion 31 bridging the distance from the surface of the skin 32 to the target area 21. The external wire component portion 29 of the needle guide assembly helps in retaining and positioning the needle guide assembly 10 within the target area and ensures safety by preventing dislocation of the needle guide assembly while inserting a catheter within the target area, while seeking the center of the target. Thus, the curved end of wire helps guide the assembly within the target.

The needle guide outer cannula 12 may be secured to the elongated guide or torque wire 22 by any suitable means or method, but preferably by a securing means which compresses the outer cannula 12 to the elongated guide or torque wire 22 to provide a unitary guide assembly comprised of a wire guide portion 29 and a tubular outer cannula portion 31. This assembly increases the effective length of the tubular outer cannula, forming a guide assembly of a length substantially greater than the length of the outer cannula. Indeed, the wire must have a length at least twice the length of the surgical instrument or catheter.

It is within the scope of the present invention that the means for securing the outer cannula to the guide or torque wire may be by crimping, by rotation of the outer cannula with respect to the guide wire when the elements are ovalized or another suitable configuration, or by fastening, such as, by screwing the wire to the cannula.

After the outer cannula 12 has been compressed to about the elongated wire guide or torque wire 22, the removable hub member 20 is then removed from the proximal end 14 of the needle guide outer cannula 12 and any type of surgical instrument or catheter 34, from 4 French up to 10 French in size, can be slidably advanced over the wire external portion 29 and the needle guide outer cannula portion 31 to be positioned within the target area.

Thus, the needle guide assembly of the present invention incorporates the advantages of a short locator needle assembly to locate a target area, and a substantially longer needle guide assembly to enhance manueverability and control during placement of a tubular surgical instrument at the target area within the body. Prior art arrangements, on the one hand, used needle guide systems 40 to 45 centimeters in length which was ackward to use. Short guide systems were not suited for use in the placement of surgical tubes at a target area because of the insufficient lengths of the needle protruding from the body at the point of insertion of the needle assembly into the body. The guide assembly of the present invention has an effective length which is about twice the distance from the point of insertion of the guide cannula into the body to the target area within the body. Thus, sufficient length of the guide assembly protrudes from the body to enable the user to easily guide catheters or other instruments to the target area.

It is also within the scope of the present invention that larger diameter outer cannulas may be slidably advanced or small diameter cannulas to increase the rigidity of the assembly. After the outer cannula 12 has been crimped about the guide wire 22, it is possible to slidably advance another larger diameter cannula over this crimped assembly to provide a more rigid assembly for guiding the surgical instrument or catheter to a target area. This additional cannula may, itself, be crimped to the cannula 12 and guide 22 to provide a concentrically arranged series of cannulas of increasing diameter crimped together to provide a rigid guide assembly in accordance with the present invention.

Figure 1:
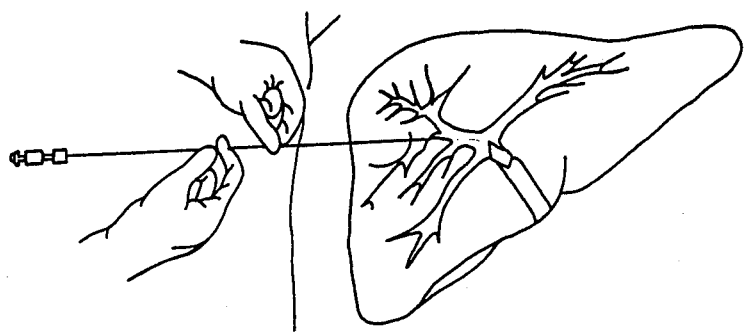
FIG. 1, labeled PRIOR ART, is a schematic cross-section through a portion of a human body demonstrating the insertion into the body of a known needle guide assembly.

The advantages of using the novel short needle guide assembly in accordance with the present invention over the prior art needle guide assemblies as shown in FIG. 1, are enhanced needle control, improved maneuverability by use of various shaped flexible tips, the ability to place longer catheters within the target area, and better visualization during insertion of the needle guide assembly into the target area. Image intensifiers can be brought closer to the patient and the target in question and the axial alignment by fluoroscopic means can be readily performed without bending the needle assembly or injuring the patient during placement of the needle guide assembly within the target area. The positioning and placement of the needle guide assembly within the target area may be confirmed using orthogonal views, injection of contrast through the needle guide outer cannula or the return of body fluid from the target area 2. As shown in FIG. 1, the prior are guide assemblies 1, require placement of an outer cannula over the locator cannula (not shown) after the location of the target area, before advancing a catheter (not shown) over the assembly wire guide. 22 to provide a concentrically arranged series of cannulas of increasing diameter crimped together to provide a rigid guide assembly in accordance with the present invention.

The advantages of using the novel short needle guide assembly in accordance with the present invention over the prior art needle guide assemblies as shown in FIG. 1, are enhanced needle control, improved maneuverability by use of various shaped flexible tips, the ability to place longer catheters within the target area, and better visualization during insertion of the needle guide assembly into the target area. Image intensifiers can be brought closer to the patient and the target in question and the axial alignment by fluoroscopic means can be readily performed without bending the needle assembly or injuring the patient during placement of the needle guide assembly within the target area. The positioning and placement of the needle guide assembly within the target area may be confirmed using orthogonal views, injection of contrast through the needle guide outer cannula or the return of body fluid from the target area 2. As shown in FIG. 1, the prior art guide assemblies 1, require placement of an outer cannula over the locator cannula (not shown) after the location of the target area, before advancing a catheter (not shown) over the assembly wire guide.

Figure 7:
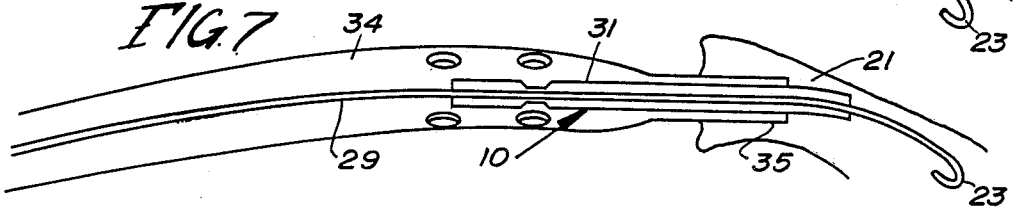
FIG. 7, illustrates use of the guide assembly in accordance with the present invention used as a guide for advancing a drainage instrument, surgical instrument or catheter into the target area.

As shown in FIGS. 4–7, when the flexible distal end 23 of the elongated or torque wire 23 has been positioned within the target, the distal end 13 of the outer cannula member 12 may be somewhat flexible to follow the curvature of the elongated guide or torque wire 22 deep into the target, as shown in FIG. 4. Additionally, as shown in FIG. 7, when the surgical instrument or catheter 34 is inserted over the guide wire portion 29 and the needle guide over cannula portion 31, the needle guide outer cannula member 12 itself acts as a guide wire in positioning the distal end 35 of the surgical or catheter instrument 34 within the target area 21 of the patient.

A further embodiment of the present invention is shown in FIGS. 8-12, wherein the needle guide assembly 10 includes a needle guide outer cannula member 12, having a distal end 13 and a proximal end 14. Attached to the distal end 13 of the outer cannula is a flexible or floppy tip portion 38, which may be comprised of a spiral of helix spring member 39 having a hollow bore 39a. However, the floppy tip portion 38 may be flexible and be constructed of metal or plastic. The tip portion may be of such a metal that it possesses a memory and have a J-shape on its distal end to facilitate guidance of the assembly within the target to optimize location in the target.

As shown in FIG. 8, the outer cannula 12 having the flexible floppy tip 38, comprised of a helix spring member 38 mounted thereon, and containing a locator needle or stylus 16 therein is inserted into the body tissue to penetrate, as way of an example, an artery or vein 40 within the body. Depending upon the target area of application, the spiral or floppy helix spring 39 is impregnated or coated with a plastic material 39a in a manner similiar to the procedure described in U.S. Pat. No. 4,004,765, which facilitates insertion of the spiral floppy tip portion 38 held rigid by the distal end 17 of the locator needle or stylus 16 into the vein or artery 40. The distal end of the locator needle or stylus 16 extends through the hollow bore 39a of the coil spring 39, maintaining it substantially rigid during insertion of the guide assembly into the body.

When a fluoroscope or other image intensifier confirms the location of the flexible floppy tip portion 38 and guide assembly 10 within the vein 40, the locator needle or stylus 16 and the hub portion 20A is unscrewed from the female hub portion mounted to the proximal end 14 of the outer cannula member 12, or described above, and the locator needle or stylus 16 is withdrawn from the outer cannula 12, the position as shown in FIG. 9, allowing the floppy tip portion 38 to orient itself within the body cavity or lumen in which it is located. Thereafter, an elongated guide or torque wire 22 is inserted through the outer cannula member 12, and through the flexible or floppy tip portion 38, spring member 39, the position as shown in FIG. 10. Thereafter, a crimping tool 27 is utilized to concentrically compress the needle guide outer cannula 12 around the guide or torque wire 22 to provide a needle guide assembly having a flexible wire portion 29 and a more rigid outer cannula portion 31, as well as a floppy and flexible helix spring portion 39, with the flexible distal end 23 of the guide or torque wire 22 extending therebeyond, the position as shown in FIG. 11. After the crimping tool 27 has compressed the needle guide cannula 12 to the guide wire 22, the hub portion 20 is removed from the proximal end 14 of the outer cannula 12 and a surgical instrument or catheter 34 is slidably advanced over the needle guide outer cannula 12, past the flexible and floppy helical spring member 38 and along the elongated guide wire 22 to position the catheter 34 or surgical instrument within the vein 40 at the obstruction or target area 21 desired. As shown in FIG. 12, the outer cannula member 12 is adapted to be slightly bent and itself act as a guide wire to facilitate advancement of the surgical instrument 34 along the guide wire assembly into the target area.

The practices of unique and novel needle guide assembly in accordance with the embodiments of the present invention require a novel method for placement of a surgical instruments or catheter at or within a target area within a human or animal body. The method of placement comprises the step of probing the body with a needle guide assembly having a needle guide outer cannula and a locator needle or stylus slidably positioned within the needle guide outer cannula. After locating and pinpointing the target area to be investigated, or surgically operated upon, the locator needle or stylus is withdrawn from the outer cannula member and an elongated guide wire is advanced within the outer cannula member 12 and into the body to locate the flexible distal end of the guide wire at or adjacent the target area. Thereafter, the outer cannula member is crimped and fixedly attached to the elongated guide wire, with the removal of the removable hub from the distal end of the outer cannula member permitting advancement of a surgical instrument or catheter member along elongated guide wire portion and outer cannula member portion to the target area to be investigated.

The utilization of a flexible or floppy helical spring member, attached to the distal end of the outer cannula member 12, provides for a smooth transition between the distal end of the outer cannula 12 and the flexible distal end 23 of the guide wire and prevents cleavage of the guide wire upon the sharp distal end of the outer cannula needle. Additionally, the positioning of a flexible floppy helical spring member 39 on the distal end 13 of the outer cannula member 12 provides for a smooth transition there between and facilitates advancement and curvature of the needle guide outer cannula 12 along the guide wire 23. This permits the needle guide outer cannula member 12, itself to function as a guide wire in facilitating placement of surgical instruments and catheters in the target area to be investigated. The tip provides manueverability to prevent penetration of the far wall of the target area.

The embodiments described above illustrate the features of the invention in a form which the inventor has found most practically suited to his uses, however, other configurations may well be generated or utilized by persons reasonably skilled in the art, and such variations and modifications are considered to be within the spirit and scope of the present invention.

I claim:

1. A needle guide set for use in the placement of tubular surgical instruments within a human or animal body, comprising:

a needle guide outer cannula;

a locator needle; and a guide wire;

said needle guide outer cannula including a hollow tubular member having a distal end and a crimpable proximal end portion;

said locator needle having a proximal end and a distal end with a sharp piercing tip portion, said locator needle constructed and arranged to be removably positioned within said needle guide outer cannula with its proximal end located adjacent to the proximal end portion of said needle guide outer cannula and with said sharp tip portion projecting from said distal end of said needle guide outer cannula to facilitate penetration of the said body by said needle guide outer cannula and the positioning of the distal end of said needle guide outer cannula in the proximity of a target area within the body;

said guide wire having a distal end and a proximal end, said guide wire being insertable into the body through said needle guide outer cannula, after said locator needle has been withdrawn therefrom, said guide outer cannula proximal portion being crimped onto said guide wire to increase the effective length of said needle guide outer cannula to form a guide assembly of a length substantially greater than the length of said outer cannula for advancing the tubular surgical instrument to the target area.

2. The needle guide set according to claim 1 wherein said locator needle corresponds in length to the length of said outer cannula and wherein the length of said guide wire is substantially greater than the length of said outer cannula.

3. The needle guide set according to claim 1, wherein the length of said guide wire is at least twice the distance from the outer surface of the body of the point of insertion of said outer cannula to the target area.

4. The needle guide set according to claim 1, which further includes at least one additional hollow tubular cannula member adapted to be telescopically positioned about said guide assembly and secured thereto.

5. The needle guide set according to claim 1 wherein said guide wire is of a length of at least twice the length of the surgical instrument to be placed.

6. The needle guide set according to claim 1 wherein said needle guide outer cannula includes a hub member removably attached to said needle guide outer cannula near the proximal end thereof.

7. The needle guide set according to claim 1 wherein said outer cannula includes a hollow, flexible tip portion at its distal end adapted to receive said distal end of said locator needle when said locator needle is positioned within said outer cannula.

8. The needle guide set according to claim 7, wherein said flexible tip portion comprises a coil spring.

9. The needle guide set according to claim 8 wherein said flexible tip portion further comprises a thin polymer catheter coating or covering on said coil spring.

10. A needle guide assembly for use in the placement of tubular surgical instruments within a human or animal body, comprising:

a needle guide outer cannula means including a hollow tubular member having a distal end and a proximal end, said needle guide outer cannula means adapted for penetration of the body and positioning of its distal end in the proximity of a target area within the body;

a guide wire having a distal end and a proximal end, said guide wire positioned within said needle guide outer cannula to locate its distal end in the proximity of the target area within the body, the length of said guide wire being at least twice the distance from the outer surface of the body at the point of insertion of said outer cannula to the target area, and said needle guide outer cannula being crimped for securing said needle guide outer cannula to said guide needle increasing the effective length of said outer cannula to form a unitary guide assembly of a length substantially greater than the length of the outer cannula for advancing a surgical tubular instrument to the target area.

11. The needle guide assembly according to claim 12 wherein said needle guide outer cannula is of a length in the range of about fifteen centimeters to about twenty centimeters, and said guide wire is of a length in the range of about thirty-five centimeters to about forty-five centimeters.

12. A method for placement of a tubular surgical instrument at a target area within a human or animal body comprising the steps of:

probing the body with a locator needle assembly including a short locator needle extending within a needle guide outer cannula to locate a target area within the body;

withdrawing the locator needle from the needle guide outer cannula when the target area has been located;

inserting a guide wire through the needle guide outer cannula into the body to locate its distal end near the target area;

securing the needle guide outer cannula to the guide wire to form a needle guide assembly of a length substantially greater than the length of the locator needle assembly; and using the needle guide assembly to advance a tubular surgical instrument to the target area.

13. The method according to claim 12 wherein forming the needle guide assembly includes the step of crimping the needle guide outer cannula to the guide wire.

14. The method according to claim 13 wherein the step of inserting the guide wire into the body includes advancing the needle guide outer cannula and guide wire further into the body prior to crimping of the needle guide outer cannula to the guide wire.

15. The method according to claim 12 wherein the needle guide outer cannula has a removable hub attached to its proximal end serving as a finger grip to facilitate insertion of the guide wire into the body through the needle guide outer cannula, and wherein the step of inserting the guide wire into the needle guide outer cannula further comprises removing the hub from the needle guide outer cannula after the guide wire is positioned with its distal end near the target area.

16. The method according to claim 12 wherein the guide wire is at least twice the length of the surgical instrument to be placed.

17. The method according to claim 12 further including the step of positioning at least one additional hollow tubular cannula about the needle guide outer cannula and securing the same together.

18. A method for placement of a tubular surgical instrument at a target area within a human or animal body comprising the steps of:

probing the body with a needle guide means to locate a target area within the body;

securing to the needle guide means a guide wire of a length substantially greater than the length of said needle guide means to increase the effective length of the needle guide means while the needle guide means remain in place with its distal end located within the body at the target area located;

and using the needle guide means with the guide wire secured thereto to advance a tubular surgical instrument to the target area.

19. The method according to claim 18 wherein securing to the needle guide means of the guide wire includes crimping the needle guide means to concentrically compress the needle guide means around the guide wire.

20. A needle guide assembly for use in the placement of tubular surgical instruments within a human or animal body, comprising;
   a needle guide outer cannula means including a hollow tubular member having a distal end and a proximal end portion, said proximal end portion having means for securing said tubular member to a guide wire, said needle guide outer cannula means being adapted for penetration of the body and positioning of said distal end in the proximity of a target area within the body;
   a guide wire having a distal end and a proximal end, the length of said guide wire being greater than the length of said outer cannula, said guide wire extending through said needle guide outer cannula with its distal end located in the proximity of the target area within the body and said securing means adapted to connect said hollow tubular member to said guide wire for securing said needle guide outer cannula to said guide wire to form a unitary needle guide assembly of a length greater than the length of the outer cannula for advancing a surgical tubular instrument to the target area 21. A needle guide assembly according to claim 20 wherein said outer cannula means is concentrically compressed about and to said guide wire.

22. The needle guide assembly according to claim 20 wherein said outer cannula means includes a hollow, flexible tip portion secured to said tubular member at its distal end for maintaining said distal end of said tubular member in the proximity of the target area.

23. The needle guide assembly according to claim 22 wherein said flexible tip portion comprises a coil spring.

24. The needle guide assembly according to claim 23 wherein said flexible tip portion further comprises a thin polymer catheter coating or covering on said coil spring.

* * * * *